United States Patent
Garoff et al.

(10) Patent No.: US 6,200,923 B1
(45) Date of Patent: Mar. 13, 2001

(54) POLYMERIZATION CATALYST COMPOSITION CONTAINING MAGNESIUM, TITANIUM, HALOGEN, AND CARBOXYLIC ACID ESTER

(75) Inventors: Thomas Garoff, Helsinki; Timo Leinonen, Tolkkinen; Sirpa Ala-Huikku, Helsinki, all of (FI)

(73) Assignee: Borealis Technology Oy, Porvoo (FI)

( * ) Notice: Subject to any disclaimer, the term of this patent is extended or adjusted under 35 U.S.C. 154(b) by 0 days.

(21) Appl. No.: 09/155,446
(22) PCT Filed: Mar. 26, 1997
(86) PCT No.: PCT/FI97/00192
§ 371 Date: Nov. 30, 1998
§ 102(e) Date: Nov. 30, 1998
(87) PCT Pub. No.: WO97/36939
PCT Pub. Date: Oct. 9, 1997

(30) Foreign Application Priority Data

Mar. 29, 1996 (FI) .......................................... 961457

(51) Int. Cl.[7] .............................. B01J 31/00; B01J 37/00; C08F 4/02; C08F 4/60; C08F 4/44
(52) U.S. Cl. ........................ 502/127; 502/107; 502/111; 502/132; 502/133; 526/124.9
(58) Field of Search ................... 526/124.9; 502/107, 502/111, 127, 132, 133

(56) References Cited

U.S. PATENT DOCUMENTS

| | | | |
|---|---|---|---|
| 5,100,849 | * | 3/1992 | Miya et al. ........................ 502/111 |
| 5,188,999 | * | 2/1993 | Duranel et al. ................... 526/124.9 |
| 5,710,229 | * | 1/1998 | Garoff et al. ........................ 502/127 |

FOREIGN PATENT DOCUMENTS

| | | | | |
|---|---|---|---|---|
| 27 44 559 | * | 4/1978 | (DE) | ..................................... 502/127 |
| 0488537 | | 6/1992 | (EP) | . |
| 0 543 227 | * | 5/1993 | (EP) | ................................. 526/124.9 |
| 2049709 | | 12/1980 | (GB) | . |

OTHER PUBLICATIONS

C.B. Yang et al., Eur. Polym. J., vol. 30, No. 2, pp. 205–214, 1994.*
Chemical Abstract, vol. 112 (1990), 236033v JP Kokai 02–20510.
Chemical Abstract, vol. 120 (1994), 135220p Eur. Polym J. 1994, 30 (2) 205–14.
Chemical Abstract, vol. 118 (1993) 83975 a=CS 271589.

* cited by examiner

Primary Examiner—Mark L. Bell
Assistant Examiner—J. Pasterczyk
(74) Attorney, Agent, or Firm—Birch, Stewart, Kolasch & Birch, LLP

(57) ABSTRACT

A novel soluble composition containing magnesium, titanium, a halogen and a carboxylic acid ester has been invented. The composition has mainly the composition according to Formula (I):

$$(MgX^3_2)_x TiX^4_4 (R(COOR')_n)_y \qquad (I)$$

wherein $X^3$ is a halogen, $X^4$ is a halogen, $R(COOR')_n$ is a carboxylic acid higher alkyl ester containing at least 8·n carbon atoms, wherein R is an n-valent substituted or unsubstituted $C_1$–$C_{34}$ hydrocarbon group, R' is a $C_1$–$C_{20}$ alkyl group, and n is an integer from 1 to 4, x is between 0.5 and 4.0, and y is between 0.8/n and 2.4/n.

50 Claims, 2 Drawing Sheets

The MFR2 values and activity values of the examples

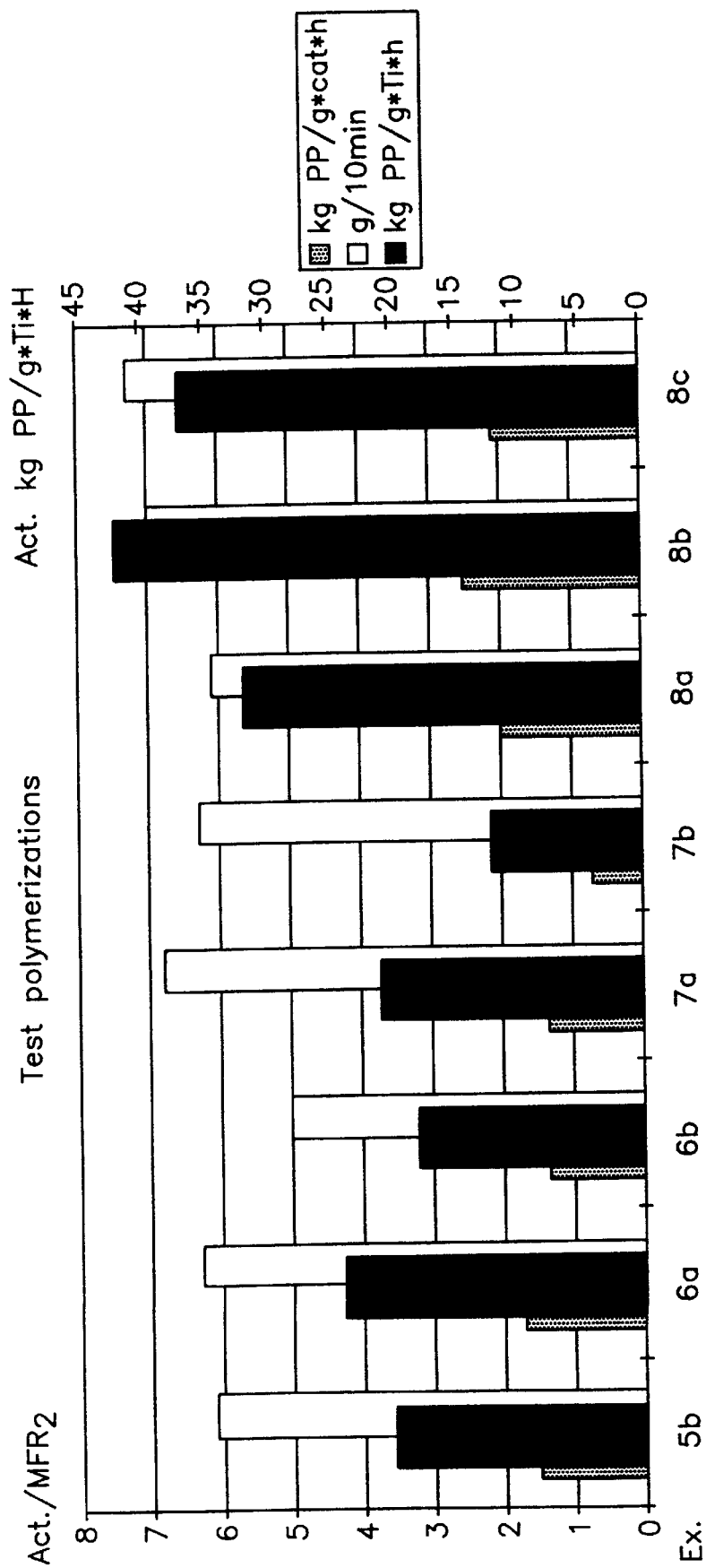

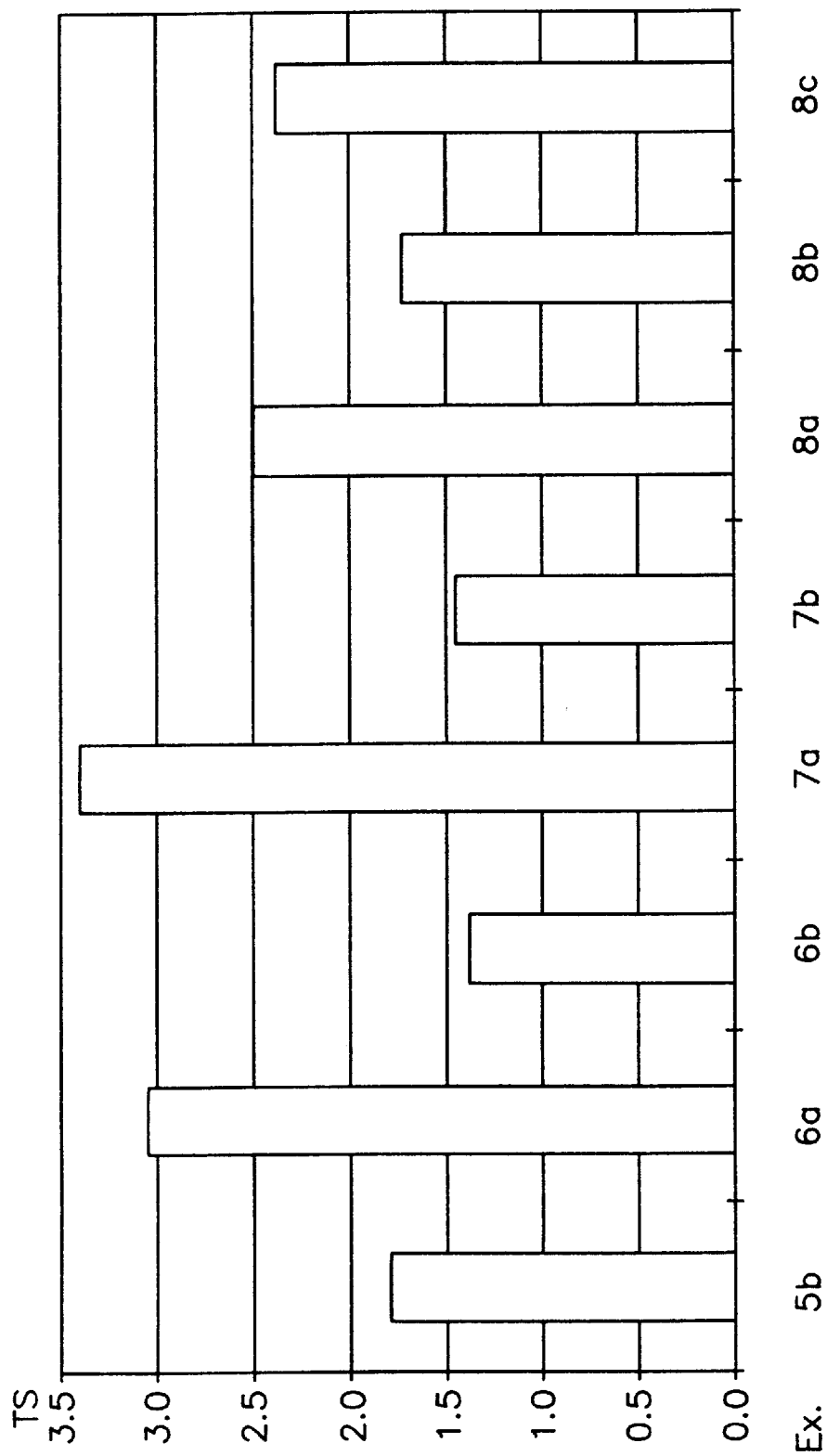

POLYMERIZATION CATALYST COMPOSITION CONTAINING MAGNESIUM, TITANIUM, HALOGEN, AND CARBOXYLIC ACID ESTER

This application claims the benefit under 35 U.S.C. §371 of prior PCT International Application No. PCT/FI97/00192 which has an International filing date of Mar. 26, 1997 which designated the United States of America, the entire contents of which are hereby incorporated by reference.

FIELD OF THE INVENTION

The invention relates to a composition containing magnesium, titanium, a halogen and a carboxylic acid ester, a process for its preparation, its use, and products obtained through its use.

BACKGROUND OF THE INVENTION

Polymerization catalysts, and in particular polymerization catalysts of the Ziegler-Natta type, currently comprise typically an inert support on which the actual active catalyst component, or a mixture or complex made up of catalytic compounds, is deposited. The chemical composition of such a heterogenous catalyst system, its surface structure, morphology, particle size, and particle size distribution are very important for the activity of the catalyst and for the properties of the polymer obtained through the use of the catalyst. By using a very active catalyst it is possible to produce a polymer from which, owing to its purity, it is not necessary to remove catalyst residues.

Heterogenous catalyst systems of the type referred to above are currently often made up of a magnesium-based support which has been treated with a transition metal compound of the titanium halide type and often also with an electron donor compound. It is also known that the support may be given an advantageous chemical composition, surface structure, morphology, particle size, and particle size distribution by allowing it to crystallize as a complex of some of its crystal solvents.

In the process according to EP publication 65700 and U.S. publication 4,421,674, a titanium halide is reacted with a magnesium chloride catalyst in the form of microspheres, whereafter the reaction product particles are recovered by physical means and are mixed together with an organometallic cocatalyst compound. FI patent application 862459 discloses a process for the preparation of a support wherein the support complex made up of a support and a crystal solvent is melted to form a clear liquid. When the liquid is directed through a nozzle and an atomization chamber into a crystallization chamber cooled with a cold nitrogen gas, the support complex will crystallize as small spherical particles. When the support pre-treated in this manner is contacted with a titanium halide, a large amount of catalytically active complexes between $MgCl_2$ and the titanium halide are formed on the surface of the support as the crystal solvent is eliminated.

SUMMARY OF THE INVENTION

Now, a new composition, active in the polymerization of e.g. ethylene, propylene and other α-olefins, has been invented, which composition contains magnesium, titanium, a halogen and a carboxylic acid ester and occurs in a soluble form. By solubility of the composition is meant in the present publication, its solubility at least in the synthesis mixture used in its synthesis, in the titanium tetrahalide used in the synthesis, and/or in an organic dissolving substance, such as toluene, used in the synthesis. The soluble composition according to the invention is mainly characterized in that it is soluble at least in a liquid titanium tetrahalide and/or an organic dissolving substance ($S^1$), and that it has a chemical composition according to the following formula (I):

$$(MgX^3{}_2)_x TiX^4{}_4 (R(COOR')_n)_y \qquad (I)$$

wherein $X^3$ is a halogen, $X^4$ is a halogen, $R(COOR')_n$ is a carboxylic acid higher alkyl ester containing at least 8·n carbon atoms, wherein R is an n-valent substituted or un-substituted $C_1$–$C_{34}$ hydrocarbon group, R' is a $C_1$–$C_{20}$ alkyl group, and n is a number between 1 and 4, x is between 0.5 and 4, and y is between 0.8/n and 2.4/n. In formula (I), the molar amount of $TiX^4{}_4$ is basically about 1.

It has thus been realized that, in deviation from prior art, it is possible to produce a soluble composition composed of a magnesium halide, a titanium halide and a carboxylic acid ester. Such a product has not been prepared, isolated, analyzed or tested previously.

BRIEF DESCRIPTION OF THE DRAWINGS

FIG. 1 illustrates melt flow rate $MFR_2$ values and activity values described in the Examples.

FIG. 2 illustrates TS values described in the Examples.

DETAILED DESCRIPTION OF THE INVENTION

According to one preferred embodiment, the carboxylic acid ester $R(COOR')_n$ is a carboxylic acid alkyl ester having at least 12 carbon atoms and, more preferably, such an α,β-unsaturated carboxylic acid $C_6$–$C_{20}$ alkyl ester. Even more preferably, the carboxylic acid ester is an aromatic carboxylic acid $C_6$–$C_{20}$ alkyl ester, most preferably a phthalic acid di-$C_6$–$C_{20}$ alkyl ester, preferably a phthalic acid di-$C_8$–$C_{14}$ alkyl ester, such as di-octylphthalate, di-nonylphthalate, di-decylphthalate, di-undecylphthalate, di-dodecylphthalate, di-tri-decylphthalate, di-tetradecylphthalate.

As was mentioned above, the novel soluble composition according to the present invention is based, at least in part, on molecules the previous combinations of which have been insoluble and have thus formed heterogenous catalysts or heterogenous catalyst components.

The first molecule in the composition according to the invention is a magnesium dihalide $MgX^1{}_2$. It is preferable that $X^1$ is chlorine, i.e. that the magnesium halide in the composition is magnesium dichloride.

Furthermore, it is preferable that the halogen $X^2$ in the titanium halide $TiX^2{}_4$ in the composition is chlorine, i.e. that the titanium halide is titanium tetrachloride.

The invention thus provides a soluble composition based on magnesium dichloride and titanium tetrachloride.

Furthermore, the composition is such that there may be 0.6–4.0 magnesium halide molecules per one titanium halide molecule. Cf. Formula (I) above, wherein x is between 0.6 and 4.0. A preferred number (x) of magnesium halide molecules in the composition according to the invention is 0.7–3.0.

The solubility of the composition according to the invention seems to be due to the fact that the quality and quantity of the donor facilitates the salvation or dissolving of the composition. As was stated above in connection with Formula (I), the number y of molecules of carboxylic acid alkyl ester in the composition is between 0.8/n and 2.4/n, wherein n is the number of carboxyl groups. y is preferably between 1.0/n and 2.4/n. Most preferably n=2, in which case y=0.5–1.2.

A preferred soluble composition according to Formula (I) is one having the formula (II)

$$(MgCl_2)_x \cdot TaCl_4 \cdot (Ph(COOR^2)_2)_y \qquad (II)$$

wherein x is 0.5–3.0 and y is 0.5–1.2; Ph stands for orthophenylene; and $R^2$ stands for a $C_6$–$C_{20}$ alkyl, preferably a $C_8$–$C_{14}$ alkyl.

Even more preferable is a soluble complex having the approximate formula (III):

$$(MgCl_2)_x \cdot TiCl_4 \cdot (di\text{-}C_8\text{-}C_{14}\text{-alkylphthalate}) \qquad (III)$$

wherein x is 0.5–3.0.

Very good results have been obtained, for example, in preparing a compound according to the general formula (IV):

$$(MgCl_2)_x \cdot TiCl_4 \cdot (di\text{-undecylphthalate}) \qquad (IV)$$

wherein x is 0.5–3.0.

The composition according to the invention may be a mixture of molecules, a mixture of a molecule/molecules and a complex/complexes, a single complex, or a mixture of complexes. By a complex is meant in this connection a higher ordinal number compound composed of molecules in contrast to first ordinal number compounds composed of atoms. Cf. Römpps Chemie-Lexicon, 7. Auflage, 1972, Teil 3, S. 1831. The composition according to the invention is composed of three types of molecules, $MgX^1_2$, $TiX^2_4$, and $R(COOR')_n$. The decimal numbers in the formulae indicate that what is in question is a mixture of molecules and/or complexes, having an average molecular composition indicated by the decimal numbers.

The invention also relates to a process for preparing a composition containing magnesium, titanium, a halogen and a carboxylic acid ester, wherein a complex $MgX^1_2 \cdot cR^1OH$, wherein $X^1$ is a halogen, $R^1$ is a $C_1$–$C_{20}$ alkyl and c is 2.0–6.4, a titanium halide $TiX^2_4$, wherein $X^2$ is a halogen, and a carboxylic acid ester are contacted and reacted at a certain temperature. The process is mainly characterized in that said composition is prepared in liquid form by using (a) as said carboxylic acid ester a carboxylic acid alkyl ester having at least 8·n carbon atoms and being expressed by the following Formula (V)

$$R(COOR')_n \qquad (V)$$

wherein R is an n-valent substituted or unsubstituted $C_1$–$C_{34}$ hydrocarbon group, R' is a $C_1$–$C_{20}$ alkyl group, and n is a number between 1 and 4;
(b) a molar ratio $R(COOR')_n/MgX^1_2 \cdot cR^1OH$, which is $\geq$ about 0.8/n;
(c) a molar ratio $TiX^2_4/MgX^1_2 \cdot cR^1OH$, which is $\geq$ approx. c;
(d) optionally an organic dissolving substance S; and
(e) as said certain temperature a value between 40 and 200° C.

In this connection, also, it is preferable that said carboxylic acid ester $R(COOR')_n$ is a carboxylic acid ester having at least 12 carbon atoms, more preferably such a carboxylic acid $C_6$–$C_{20}$ alkyl ester. Even more preferably said carboxylic acid ester $R(COOR')_n$ is an α,β-unsaturated carboxylic acid $C_6$–$C_{20}$ alkyl ester, more preferably an aromatic carboxylic acid $C_6$–$C_{20}$ alkyl ester, most preferably a phthalic acid $C_6$–$C_{20}$ alkyl ester, and most preferably a phthalic acid $C_8$–$C_{14}$ alkyl ester.

The halogen $X^1$ of the complex $MgX^1_2 \cdot cR^1OH$ is preferably chlorine and, independently, the group $R^1$ in the alcohol $R^1OH$ of the complex is preferably a $C_1$–$C_{12}$ alcohol and more preferably a $C_2$–$C_8$ alcohol, such as ethanol. Most preferably the complex $MgX^1_2 \cdot cR^1OH$ used in the process is the complex $MgCl_2 \cdot cC_2H_5OH$, wherein c is 2–6, preferably about 3. It can thus be seen that, in accordance with the present invention, a usable soluble composition can be prepared from the complex of magnesium chloride and ethanol, known from the heterogenous catalysis.

It is preferable that the halogen, i.e. $X^2$, in the titanium halide is chlorine, in which case there will be a titanium tetrachloride molecule in the composition. In a reaction between the complex $MgX^1_2 \cdot cR^1OH$ and a titanium halide there may be formed small amounts of titanium trichloride alkoxide, part of which may remain as a small portion of the final composition. The patent's scope of protection also covers a composition containing small amounts ($\leq$ about 10 molar % of the total amount of titanium) of such a component and a process for preparing such a composition.

The ratio $TiX^2_4/MgX^1_2 \cdot cR^1OH$ is preferably $\geq$ about 1.7c, more preferably between 10 and 100, most preferably between 20 and 50, when c is between 2.0 and 6.4. The process temperature is preferably between 60 and 140° C., most preferably between 80 and 120° C.

As is evident from the above, the molar ratio of the carboxylic acid ester to the magnesium halide may vary widely. The ratio depends very much also on other factors, such as the donor used, the solvents used, the solvent amount used, and the temperature used in the preparation of the composition. All of these parameters can be adjusted empirically so that the ester content in the composition will be sufficient and suitable for producing a soluble composition.

In the process according to the invention it is preferable to use as the carboxylic acid ester a compound according to the formula $Ph(COOR^2)_2$, wherein Ph stands for orthophenylene and $R^2$ stands for a $C_6$–$C_{20}$ alkyl, preferably a $C_8$–$C_{14}$ alkyl, and preferably a molar ratio of $R(COOR')_n/Mg$, which is $\geq$ about 1/n and most preferably between 1/n and 20/n.

According to one embodiment, said complex $MgX^1_2 \cdot nR'OH$, said titanium tetrahalide $TiX^2_4$ and said carboxylic acid ester $R(COOR')_n$ are contacted with an organic compound S, preferably a chlorinated hydrocarbon and/or an aromatic hydrocarbon, most preferably an aromatic hydrocarbon such as toluene, which dissolves said reaction product. The molar ratio $TiX^2_4/S$ is in this case preferably between 0.5 and 20, most preferably between 1 and 6.

According to one embodiment, the contacting step in the process precedes the heating step. According to one embodiment of the invention:

(a) the first complex $MgX^1_2 \cdot cR^1OH$, the titanium halide $TiX^2_4$ and optionally the dissolving substance S are contacted, whereby a first contact product is formed;
(b) the first contact product of step (a) is contacted with said carboxylic acid ester $R(COOR')_n$, whereby a second contact product is formed.

In step (b) the carboxylic acid ester $R(COOR')_n$ is added to the contact product preferably gradually, preferably within 10–60 minutes. In this case the heating of the forming second contact product can be carried out gradually in said step (b) during the adding of the carboxylic acid ester, for example so that the adding is started at room temperature, about 20° C., and at the end of the adding a temperature of at least about 50° C. is reached.

As the procedure has been in the embodiment examples 1 and 2 appended to the present application, the composition may be left in solution and may, when so desired, be used as a homogenous catalyst or as a homogenous starting substance for other catalysts. According to one embodiment, however, the process according to the invention comprises an additional step, in which the dissolved composition is isolated by precipitation. In this case the precipitation can be carried out either by cooling, for example to room temperature, a reaction solution in which the composition is in solution largely in an excess of the titanium halide $TiX^2_4$, whereafter the precipitated composition is separated from the rest of the reaction solution, or by adding to a reaction solution in which the composition is in solution largely in an excess of the titanium halide $TiX^2_4$ a precipitating hydrocarbon, preferably a $C_5$–$C_{10}$ alkane such as heptane, either all at once, gradually or periodically, whereafter the precipitated composition is separated from the rest of the reaction solution.

A novel soluble composition containing magnesium, titanium, a halide and a carboxylic acid ester and a process for the preparation thereof has been described above. The invention also relates to the use of said composition, or a composition prepared by said process, as a catalyst in the polymerization, i.e. homo- or copolymerization, of ethylenically unsaturated monomers and preferably ethylene, propylene and other α-olefins. Said composition may, when necessary, be used as a catalyst together with an organometallic compound of a metal of any of groups 1, 2, 12 or 13 (IUPAC 1990) of the Periodic Table of the Elements, used as a cocatalyst.

Another area of use of the composition according to the invention relates to the preparation of polymerization catalysts. Thus the composition according to the invention can be used as an initial substance or as an intermediate in the preparation of catalysts or catalyst components intended for the polymerization, i.e. homo- or copolymerization, of ethylenically unsaturated monomers, such as ethylene and other α-olefins. Finally invention relates to polymerization products, i.e. polymers, catalyzed by using a composition according to the invention and to catalysts or catalyst components prepared from a composition according to the invention.

The present publication thus describes a new soluble magnesium halide—titanium halide—ester composition having catalytic polymerization activity. The invention is illustrated below with examples, of which the first two concern the preparation of a homogenous (catalyst) composition in solution, the third example describes the bringing of the (catalyst) composition to solid form, and the fourth example concerns the preparation of a (catalyst) composition, its bringing into a solid form, and its use for gas phase copolymerization. In examples 5 to 8, compositions based on different carboxylic acid esters have been prepared, analyzed and tested. The following examples are only by way of illustrating the invention.

EXAMPLE 1

Preparation of a Soluble Composition 150 ml of toluene was introduced into a one-liter jacketed reactor in inert conditions at room temperature. 25.0 g of $MgCl_2 \cdot 3EtOH$ material was added into the reactor. The stirring speed of the reactor was 150 r/min. Then 300 ml of $TiCl_4$ was added.

After the slurry had been prepared, the adding of the electron don or, i.e. undecylphthalate (DUP), was started, the adding taking place gradually, while the reaction temperature was raised at the same time by using a temperature profile of +1.5° C./min. The added DUP amounts and the corresponding adding temperature are shown in Table 1.

TABLE 1

Adding of DUP to the reation mixture and the corresponding temperatures. The total amount of DUP added was 20 ml (0.04 mol)

| Time from the first addition (min) | Temperature of the mixture (° C.) | Added DUP (ml) |
|---|---|---|
| 0 | 21.8 | 5.0 |
| 6 | 22.9 | 5.0 |
| 14 | 24.3 | 5.0 |
| 20 | 28.5 | 5.0 |

When the temperature of the mixture was raised further, the color of the liquid became darker and slightly brownish red. When a temperature of 129.0° C. had been reached, the reaction mixture was kept at that temperature for one hour. Thereafter the reaction mixture was filtered to indicate any undissolved ingredient. However, the dissolving had been substantially complete.

Finally 300 ml of $TiCl_4$ was added. The obtained solution was completely clear, and no solids were visible.

EXAMPLE 2

Preparation of Another Soluble Composition 150 ml of toluene was introduced into a one-liter jacketed reactor in inert conditions at room temperature. 25.0 g of $MgCl_2 \cdot 3EtOH$ material was added into the reactor. The speed of the stirrer was 150 r/min. Next, 300 ml of $TiCl_4$ was added. The liquid in the mixture became dark red. After the dispersion had been prepared, the adding of the donor, i.e. di-undecylphthalate (DUP) was started, the reaction temperature being at the same time raised using a temperature profile of +1.5° C./min. The DUP amounts added and the corresponding adding temperatures are shown in Table 2. In total, 25 ml of DUP was added.

TABLE 2

Adding of DUP to the reaction mixture and the corresponding adding temperatures. The total amount of DUP added was 25 ml (0.05 mol)

| Time from the first addition (min) | Temperature of the mixture (° C.) | Added DUP (ml) |
|---|---|---|
| 0 | 23.3 | 5.0 |
| 8 | 25.2 | 5.0 |
| 16 | 29.9 | 5.0 |
| 22 | 35.1 | 5.0 |
| 30 | 43.1 | 5.0 |

The reaction mixture had not yet dissolved immediately after the adding of DUP. The stirring speed was 160 r/min. When the temperature was raised further, the liquid in the mixture became darker and somewhat reddish brown. When the temperature was 129.3° C., the reaction mixture was very dark. It was noted that the catalyst components had dissolved. This showed that all solid magnesium chloride insoluble in titanium tetrachloride and toluene had disappeared and a soluble composition had formed.

EXAMPLE 3

Preparation, Separation and Analysis of a Composition 75 ml of toluene was introduced into a one-liter jacketed reactor in inert conditions at room temperature. 12.5 g of MgCl$_2$.3EtOH was added into the reactor. The stirring speed was 150 r/min. The temperature was lowered to 0° C. Thereafter 150 ml of TiCl$_4$ was added, whereupon the mixture became dark red. Thereafter the temperature of the mixture was raised at a rate of +0.25° C./min. When the temperature was 22.6° C., 12.5 ml of the donor, i.e. di-undecylphthalate (DUP), was added. Thereafter the reaction temperature was raised at a rate of +1.5° C./min.

Immediately upon the adding of the donor the mixture still contained undissolved material. The stirring speed was 200 r/min. When the temperature was raised further, the mixture became dark and turned slightly more brick red. When the temperature was 94.7° C., the reaction mixture was very dark. All of the catalyst components had dissolved. This showed that a soluble composition had formed.

The solution was transferred into a one-liter vessel and was allowed to cool to room temperature, at which time the composition was allowed to precipitate and deposit on the bottom of the vessel. Thereafter the liquid was syphoned off as precisely as possible.

The precipitated composition was washed twice with 150 ml of heptane at room temperature, whereafter the composition was dried in a nitrogen stream until it was completely dry. The chemical composition of the product was analyzed. The results of the analysis are shown in Table 3.

TABLE 3

Chemical composition of the solidified composition

| Component | wt. % | mol. % | mol/mol Ti |
|---|---|---|---|
| Mg | 4.4 | 40.61 | 1.55 |
| Ti | 5.6 | 26.17 | 1 |
| EtO- as EtOH | 1.6 | 7.96 | 0.30 |
| DEP | 0.17 | 0.171 | 0.006 |
| DUP | 43.6 | 25.07 | 0.96 |

Hardly any di-ethylphthalate was found in the composition. Instead, it contained a small amount of ethoxide EtO-, which originated in the reaction between TiCl$_4$ and the first complex MgCl$_2$.3EtOH. Calculated as ethanol EtOH, the concentration of EtOH was 1.6%, i.e. 7.96 mol. %. However, the results show that hardly any inter-esterification had occurred between di-undecylphthalate and ethanol. Although the composition contained slightly less magnesium than required by a precise composition, its approximate formula was as follows:

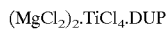

(MgCl$_2$)$_2$.TiCl$_4$.DUP

An X-ray diffraction spectrum was also taken of the solid composition. The diffraction pattern has a typical peak at 50° 2theta and a halo between 30° and 35° 2theta. In addition, there is a considerable second halo between 15° and 22° 2theta. This second halo does not appear in the corresponding X-ray diffraction of a heterogenous MgCl$_2$-based Ziegler-Natta catalyst. By a heterogenous MgCl$_2$-based Ziegler-Natta catalyst is meant here a MgCl$_2$/TiCl$_4$/internal electron donor catalyst.

The results show that the composition prepared had a clearly demonstrable chemical composition and a distinct X-ray diffraction spectrum.

EXAMPLE 4

Use of the Composition as a Polymerization Catalyst 200 ml of toluene was introduced into a one-liter jacketed reactor in inert conditions. 25.0 g of MgCl$_2$.3EtOH material was added into the reactor. Thereafter, 25.0 ml of di-undecylphthalate (DUP) was added to the reaction mixture. The reaction solution was stirred for 30 min at room temperature (22° C.). The stirring speed was 150 r/min.

After the reaction suspension had stabilized for 30 min, 300 ml of TiCl$_4$ was added. Thereafter the temperature was raised rapidly to 100° C. At 86° C. all the components had already dissolved, i.e. reacted to form a soluble composition.

When the mixture, i.e. the solution, in the reactor was completely clear, the composition was precipitated out from the solution by adding heptane to the solution. The heptane amounts added are shown in Table 4, together with the temperature of the reaction solution. In order to avoid a drastic cooling effect, the heptane was preheated to 90° C. before the adding.

TABLE 4

Heptane amounts added and reaction solution temperatures used

| Adding time (min) | Reaction solution temperature (° C.) | Heptane amount added (ml) |
|---|---|---|
| 0 | 105 | 150 |
| 15 | 93 | 50 |
| 20 | 85 | 50 |

After the adding of the heptane the reaction solution was allowed to cool to 65° C., and the composition was allowed to settle on the bottom. Thereafter the solution was filtered off and the catalyst composition was washed four times with 400 ml of heptane. Finally the catalyst composition was dried in the nitrogen stream. The chemical composition of the catalyst composition was measured. The results of the analysis are shown in Table 5.

TABLE 5

Chemical composition of the catalyst

| Component | Wt. % | Mol. % | mol/mol Ti |
|---|---|---|---|
| Ti | 6.1 | 22.4 | 1 |
| Mg | 8.5 | 62.0 | 2.77 |
| DUP | 40.8 | 15.2 | 0.68 |
| Phthalic acid anhydride | 0.2 | 0.35 | 0.015 |

No trans-esterified di-ethylphthalate was found in the catalyst composition. Thus the chemical composition of the catalyst composition was very close to the following:

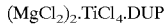

(MgCl$_2$)$_2$.TiCl$_4$.DUP

The catalyst composition was recovered for test polymerization. 20.2 mg of said catalyst composition was weighed for the copolymerization of propylene and ethylene. Tri-isobutylaluminum (TIBA) was used as a cocatalyst. The Al/Ti molar ratio was 200. Cyclohexylmethyldimethoxysilane (CMMS) was used as an external donor. The molecular weight was adjusted by adding 4 mmol of H$_2$. The cocatalyst and the external donor were pre-contacted in 30 ml of pentane before use, whereafter one half of the solution was fed directly into a gas phase reactor and the other half was pre-contacted with the catalyst composition before the adding of the catalyst. The propylene monomer feed contained ethylene comonomer 4.7%. The polymerization was carried out at a temperature of 70° C. and a total pressure of 7.4 bar for 2 hours.

25 g of copolymer was obtained as the result. The corresponding activity was 1.23 kg EP/g cat and 20.2 kg EP/g Ti. According to infrared spectra, the polymer contained ethylene units 7.8%, out of which 4.7% were in a random pattern, which caused a 60% random distribution.

This test polymerization result showed clearly that the novel composition had catalytic polymerization activity.

EXAMPLES 5–8

Preparation of a Soluble $MgCl_2.TiCl_4.D_1$ Composition, wherein $D_1$ Stands for a Phthalic Acid Higher Alkyl Ester These examples describe the preparation of a $MgCl_2.TiCl_4.D_1$ catalyst composition by using different types of long-chain alkyl esters of phthalic acid. Four phthalic acid esters ($D_1$) were used in the examples, i.e. di-2-ethylhexylphthalate (DOP), di-isodecylphthalate (DIEP), di-undecylphthalate (DUP), and di-tridecylphthalate (DTDP). The polymerization active complexes were analyzed and their efficiency in bulk homopolymerizations of propylene were investigated. In this context, the word "complex" can be used of the composition according to the invention without limiting the protective scope, since the molecular composition of the product is very uniform.

EXPERIMENTAL SECTION

Synthesis of the $MgCl_2.TiCl_4.D_1$ Composition 12.5 g (131.4 mmol) of $MgCl_2.3EtOH$ complex was fed into a thermostat-controlled glass reactor. The $MgCl_2.3EtOH$ complex had been prepared by spray crystallization. 100 ml (0.94 mol) of toluene and thereafter 150 ml (1.37 mol) of titanium tetrachloride $TiCl_4$ were added. All of the additions were done at room temperature. The molar ratio $TiCl_4$/toluene was 3:2. Last, 65.7 mmol of the phthalic acid ester concerned was added. The molar ratio of the ester to magnesium was 0.5. The temperature was raised in the course of an hour to 100° C., and the reaction mixture was kept at that temperature for 30 min in order to obtain a clear solution which no longer contained any solid matter. Thus a soluble $MgCl_2.TiCl_4.DUP$ composition was formed. The molar ratio of the titanium tetrachloride $TiCl_4$ to the composition was about 20. Thereafter the solution was allowed to cool to about 90° C., and 550 ml of cold heptane was added. Thereby the temperature was lowered to about 70° C., and the composition precipitated in the form of a yellow mass. After the solution composed of toluene, titanium tetrachloride $TiCl_4$ and titanium trichloride ethoxide $TiCl3OR$ had been removed by decanting, the solid composition was washed three times with 650 ml of heptane. The product was dried with nitrogen.

The product was analyzed for Ti, Mg, Cl, phthalic acid ester and any phthalic acid mixed esters, as well as for phthalic acid anhydride. The product was also analyzed for its ethanol content, which was considered to be derived from titanium trichloride ethoxide $TiCl_3.OEt$ remaining in the product. In addition, the composition was re-dissolved in 500 ml (4.7 mol) of toluene in order to obtain better morphology. In order to improve solubility, the temperature was raised to 90° C. When a clear solution had been produced, it was allowed to cool in half an hour to a temperature of about 30–40° C. Thereafter 330 ml of heptane was added and the composition reprecipitated. Finally the composition was washed three times with 500 ml of heptane. After drying, the composition was analyzed in the same manner as described above.

Bulk Polymerization

Propylene was polymerized in a stirred tank reactor having a volume of 5 liters. About 0.9 ml of a triethylaluminum cocatalyst, about 0.5 ml of a 25 vol. % n-heptane solution of cyclohexylmethyldimethoxysilane (external donor) and 30 ml of n-pentane were mixed together and were reacted for 5 minutes. One-half of the obtained mixture was fed into the polymerization reactor and the other half was mixed with about 20 mg of a catalyst consisting of said composition. After five more minutes, the catalyst/TEA/external donor/n-heptane mixture was fed into the reactor. The molar ratio Al/Ti was 250 and the molar ratio Al/external donor was 10. 70 mmol of hydrogen and 1400 g of propylene were added into the reactor, and the temperature was raised within 15–30 min to 70° C. The polymerization time was 60 min, whereafter the formed polymer was removed from the reactor. The melt flow rate ($MFR_2$), bulk density (BD) and xylene-soluble total fraction (TS) were determined from the polymer.

Results

In the preparation of the composition, probably the following reactions occur in the titanium tetrachloride ($TiCl_4$)-toluene solution:

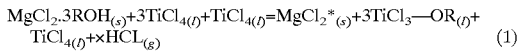

$$MgCl_2.3ROH_{(s)} + 3TiCl_{4(l)} + TiCl_{4(l)} = MgCl_2*_{(s)} + 3TiCl_3\text{—}OR_{(l)} + TiCl_{4(l)} + xHCL_{(g)} \quad (1)$$

When titanium tetrachloride $TiCl_4$ reacts with the alcohol ROH of the complex $MgCl_2.3ROH$, there forms hydrogen chloride, which leaves in the form of gas. The titanium trichloride ethoxide $TiCl_3OEt$ is first partly solid, partly in solution in an excess of titanium tetrachloride, but as the temperature rises, most of this titanium trichloride ethoxide dissolves. The $MgCl_2*$ releasing from its alcohol complex is in an amorphous state. Some of the titanium tetrachloride $TiCl_4$ and some of the titanium trichloride ethoxide react with the amorphous magnesium chloride $MgCl_2*$.

After a long-chain alkyl ester of phthalic acid, such as DUP, has been added, there occurs a reaction of dissolving in unreacted titanium tetrachloride $TiCl_4$:

$$2MgCl_2*_{(s)} + DUP_{(l)} + TiCl_{4(l)} + xTiCl_{4(l)} = MgCl_2TiCl_4DUP_{(l)}\text{—}x TiCl_{4(l)} \quad (2)$$

At this stage, a clear solution has formed. When heptane ($C_7$) is added, the dissolving $TiCl_4$ is eluted from the complex and the complex precipitates:

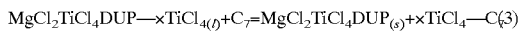

$$MgCl_2TiCl_4DUP\text{—}xTiCl_{4(l)} + C_7 = MgCl_2TiCl_4DUP_{(s)} + xTiCl_4\text{—}C_7 \quad (3)$$

Also a small amount of titanium trichloride ethoxide precipitates together with the complex. The invention relates both to a complex without titanium trichloride ethoxide and a complex which contains some titanium trichloride ethoxide. During the hydrocarbon wash, some titanium tetrachloride $TiCl_4$ and some phthalic acid higher alkyl ester DUP are removed from the complex, at a molar ratio of $TiCl_4/DUP=1:1$.

The purpose of the above explanation model is only to illustrate the invention and by no means to limit the patent protection of the invention. There may be also other explanations for the phenomena of the invention.

Preparation of Catalytic Compositions

The preparation of precipitated compositions took place without difficulty. After 15 ml of liquid $TiCl_4$ had been added to a slurry of toluene and the complex $MgCl_2.3EtOH$, the color of the slurry became red. After another 15 ml of $TiCl_4$ had been added, the color of the slurry was dark red. After the adding of the phthalic acid ester there formed a dark red solution which became completely clear when heated to 100° C. When heptane was added, a yellow precipitate formed. Upon being dried the precipitate became tarry.

All of the precipitates dissolved well in hot toluene. In most cases the morphology improved upon re-precipitation. Only when di-undecylphthalate DUP was used did re-precipitation not improve the morphology. When di-tridecylphthalate DTDP was used, two precipitates were obtained when the toluene solution was treated with heptane: one dark and coarse (cf. Example 8b) and the other lighter and more fine-grained (cf. Example 8c). The numbers of the examples, the phthalates used in them, and their outer appearance and morphology are shown in Table 6.

Chemical Composition of the Compositions

Table 7 shows the chemical composition of the compositions. In Table 8 the composition is shown as molar proportions, and in Table 9 these molar proportions are compared with the molar amount of titanium. The results show that the compositions of all of the products are close to a 1:1:1 composition, in which the numbers refer to titanium tetrachloride $TiCl_4$, magnesium chloride $MgCl_2$ and a phthalic acid higher alkyl ester $D_1$. Only in the dark coarse re-precipitate of Example 8b was the magnesium Mg content higher. Otherwise the atom ratio Mg/Ti was between 0.7 and 0.8. The amount of phthalic acid ester was even closer to the titanium amounts, the molar ratio $D_1$/Ti being in most cases between 0.8 and 0.9.

The amount of alcohol, or ethanol, reflects the amount of titanium in the form of titanium trichloride ethoxide, because the alcohol amount given by the analysis is viewed as being derived from said titanium trichloride ethoxide. In these examples the amount of alcohol is very low, which means that less than 10% of the total amount of titanium is in the form of titanium trichloride ethoxide. The amount varies between 5 and 8 mol-% of the total amount of titanium. The compositions also contain small amounts of trans-esterified phthalate, its percentage being about 10%.

There was no systematic trend as a function of the length of the phthalate alkyl chain. Instead, the results seem to be constant regardless of which phthalate alkyl was used in the synthesis of the composition.

Test Polymerization of the Compositions

All of the compositions were test polymerized in accordance with the description of the experimental section. The test polymerization results are shown in Table 10. The results are also shown in FIGS. 1 and 2. The polymer material obtained from the reactor was wool-like, and it had a low bulk density.

Activity

All of the activities were low, being between 1 and 3 kg PP/g cat composition. The activity with respect to titanium was between 20 and 40 kg PP/g Ti. With respect to magnesium Mg, a slight trend was observed that as the magnesium concentration increased, the activity increased.

Hydrogen Sensitivity

The melt flow rate $MFR_2$, which indicates the hydrogen sensitivity of the catalyst, varied only slightly, between 5 and 7. There was no systematic trend.

Bulk Densities

As was stated above, the polymer product had a poor morphology. This was to be expected, because the morphology of the catalyst is usually repeated in polymers, and if the morphology of the catalyst is indefinite, the morphology of the polymer is also indefinite. In one experiment the bulk density was only 70 kg/m³.

Xylene-soluble Total Fraction TS

Again, no systematic trend was observable between the TS values and the chain lengths of the phthalate alkyls used. There is, however, a clear difference between the TS values of polymers produced by using newly precipitated compositions and the TS values of polymers produced by using compositions which had been re-dissolved or washed with toluene. The TS values decreased clearly by more than one percentage point in those polymers which were produced by using compositions washed with toluene (cf. FIG. 2).

Summary

Examples 5–8 describe a process for the preparation of a soluble catalyst composition or catalyst complex $MgCl_2.TiCl_4.D_1$ by using long-chain alkyl esters ($D_1$) of phthalic acids. The examples show that the composition according to the invention has in the described conditions the approximate composition $MgCl_2.TiCl_4.D_1$. The catalyst complex is prepared by reacting $MgCl_2.3EtOH$ with titanium tetrachloride $TiCl_4$ in a toluene solution. After the long-chain alkyl ester of phthalic acid, such as di-undecylphthalate (DUP), has been added at a molar ratio of mg/DUP=0.5, a soluble catalyst complex forms. This catalyst complex $MgCl_2.TiCl_4.D_1$ is soluble not only in titanium tetrachloride $TiCl_4$ but also in toluene. Four different phthalic acid esters were used, i.e. di-2-ethylhexylphthalate (DOP), di-isodecylphthalate (DIDP), di-undecylphthalate (DUP), and di-tridecylphthalate (DTDP). The examples show that the solubility of the catalyst complexes formed was good. In standard tests of bulk polymerization of propylene, the activity of the complexes was between 1 and 3 kg PP/g cat complex, and the $MFR_2$ of the polymer product was between 6 and 7. The xylene-soluble total fraction (TS) was between 2 and 3%, and it dropped to below 2% when the catalyst complex had been washed with toluene.

TABLE 6

Donors in the synthesis,
carbon numbers of the donor alkyls,
and toluene washes.
DOP = di-ethylhexylphthalate,
DIDP = di-isodecylphthalate,
DUP = di-undecylphthalate,
DTDP = di-tridecylphthalate.

| Examples | Donor added | Number of C-atoms in donor chain | Toluene wash | Comment |
|---|---|---|---|---|
| 5a | DOP | 8 | No | Tar |
| 5b | DOP | 8 | Yes | Grainy tar |
| 6a | DIDP | 10 | No | Tar |
| 6b | DIDP | 10 | Yes | Grainy tar |
| 7a | DUP | 11 | No | Tar |
| 7b | DUP | 11 | Yes | Tar |
| 8a | DTDP | 13 | No | Tar |
| 8b | DTDP | 13 | Yes | Red grain fraction |
| 8c | DTDP | 13 | Yes | Yellow finer fraction |

TABLE 7

Chemical composition of the compositions

| Example | Mg wt % | Ti wt % | Cl wt % | EtOH wt % | DEP wt % | DOP wt % | EOP wt % | DIDP wt % | EIDP wt % | DUP wt % | EUP wt % | DTDP wt % | ETDP wt % | PSA wt % |
|---|---|---|---|---|---|---|---|---|---|---|---|---|---|---|
| 5a | 2.7 | 7.4 | 30.7 | 0.50 | 1.3 | 45.3 | 0.8 | | | | | | | 0.1 |
| 5b | 2.6 | 7.1 | 31.6 | 0.50 | 1.3 | 42.0 | 0.8 | | | | | | | 0.1 |
| 6a | 2.5 | 7.1 | 27.6 | 0.46 | 0.6 | | | 52.1 | 2.0 | | | | | |
| 6b | 2.8 | 7.2 | 30.1 | 0.33 | 0.7 | | | 57.1 | 2.5 | | | | | 0.1 |
| 7a | 2.3 | 6.2 | 25.5 | 0.48 | 0.2 | | | | | 45.4 | 0.4 | | | |
| 7b | 2.1 | 5.3 | 22.4 | 0.54 | 0.2 | | | | | 43.7 | 0.4 | | | |
| 8a | 3.0 | 6.1 | 25.1 | 0.53 | 0.4 | | | | | | | 56.4 | 1.6 | |
| 8b | 4.8 | 5.8 | 30.0 | 0.44 | 0.5 | | | | | | | 50.3 | 1.6 | |
| 8c | 3.4 | 5.7 | 27.0 | 0.34 | 0.4 | | | | | | | 50.7 | 1.6 | |

EOP = ethyloctylphthalate,
DEP = diethylphthalate,
EIDP = ethyl-isodecylphthalate,
EUP = ethyl-undecylphthalate,
ETDP = ethyltridecylphthalate,
PSA = phthalic acid anhydride.

TABLE 8

Molar proportions in the composition

| Example | Mg mol % | Ti mol % | Cl mol % | EtOH mol % | DEP mol % | DOP mol % | EOP mol % | DIDP mol % | EIDP mol % | DUP mol % | EUP mol % | DTDP mol % | ETDP mol % | PSA mol % |
|---|---|---|---|---|---|---|---|---|---|---|---|---|---|---|
| 5a | 0.111 | 0.155 | 0.866 | 0.011 | 0.0058 | 0.116 | 0.003 | | | | | | | 0.001 |
| 5b | 0.107 | 0.148 | 0.891 | 0.011 | 0.0058 | 0.108 | 0.003 | | | | | | | 0.001 |
| 6a | 0.103 | 0.148 | 0.778 | 0.010 | 0.0027 | | | 0.117 | 0.006 | | | | | |
| 6b | 0.115 | 0.15 | 0.849 | 0.007 | 0.0031 | | | 0.128 | 0.007 | | | | | 0.001 |
| 7a | 0.095 | 0.129 | 0.719 | 0.010 | 0.009 | | | | | 0.096 | 0.001 | | | |
| 7b | 0.086 | 0.111 | 0.632 | 0.012 | 0.009 | | | | | 0.092 | 0.001 | | | |
| 8a | 0.123 | 0.127 | 0.708 | 0.012 | 0.0018 | | | | | | | 0.106 | 0.004 | |
| 8b | 0.197 | 0.121 | 0.846 | 0.010 | 0.0022 | | | | | | | 0.095 | 0.004 | |
| 8c | 0.140 | 0.119 | 0.762 | 0.007 | 0.0018 | | | | | | | 0.096 | 0.004 | |

TABLE 9

Molar proportions of compositions in comparison to titanium

| Example | Mg molar ratio | Ti molar ratio | Cl molar ratio | EtOH molar ratio | DEP molar ratio | DOP molar ratio | EOP molar ratio | DIDP molar ratio | EIDP molar ratio | DUP molar ratio | EUP molar ratio | DTDP molar ratio | ETDP molar ratio | PSA molar ratio | Total donor amount, molar ratio |
|---|---|---|---|---|---|---|---|---|---|---|---|---|---|---|---|
| 5a | 0.72 | 1 | 5.6 | 0.07 | 0.038 | 0.75 | 0.017 | | | | | | | 0.0044 | 0.810 |
| 5b | 0.72 | 1 | 6.0 | 0.07 | 0.039 | 0.72 | 0.018 | | | | | | | 0.0045 | 0.786 |
| 6a | 0.69 | 1 | 5.2 | 0.07 | 0.018 | | | 0.8 | 0.04 | | | | | | 0.845 |
| 6b | 0.77 | 1 | 5.6 | 0.05 | 0.021 | | | 0.9 | 0.05 | | | | | 0.0045 | 0.925 |
| 7a | 0.73 | 1 | 5.6 | 0.08 | 0.007 | | | | | 0.74 | 0.01 | | | | 0.754 |
| 7b | 0.78 | 1 | 5.7 | 0.11 | 0.008 | | | | | 0.83 | 0.01 | | | | 0.853 |
| 8a | 0.97 | 1 | 5.6 | 0.09 | 0.014 | | | | | | | 0.83 | 0.033 | | 0.882 |
| 8b | 1.63 | 1 | 7.0 | 0.08 | 0.019 | | | | | | | 0.78 | 0.035 | | 0.836 |
| 8c | 0.18 | 1 | 6.4 | 0.06 | 0.015 | | | | | | | 0.80 | 0.036 | | 0.853 |

TABLE 10

Test polymerizations of compositions

| | Activity | | | | |
|---|---|---|---|---|---|
| Examples | kg PP/g*cat*h | kg PP/g*ti*h | MFR$_2$ g/10 min | BD kg/m$^3$ | TS |
| 5b | 1.5 | 20 | 6.1 | 200 | 1.81 |
| 6a | 1.7 | 24 | 6.3 | 170 | 3.04 |
| 6b | 1.3 | 18 | 5.0 | 350 | 1.39 |
| 7a | 1.3 | 21 | 6.8 | 120 | 3.39 |
| 7b | 0.6 | 12 | 6.3 | 70 | 1.46 |
| 8a | 2.0 | 32 | 6.1 | 110 | 2.49 |
| 8b | 2.5 | 42 | 7.0 | 340 | 1.74 |
| 8c | 2.1 | 37 | 7.3 | 330 | 2.39 |

What is claimed is:

1. A composition containing magnesium, titanium, a halogen and a carboxylic acid ester, wherein said composition is soluble at least in a liquid titanium tetrahalide and/or an organic substance S, and has the following chemical composition (I):

$$(MgX^3{}_2)_x TiX^4{}_4 (R(COOR')_n)_y \quad (I)$$

wherein $X^3$ is a halogen; $X^4$ is a halogen; $R(COOR')_n$ is a carboxylic acid alkyl ester containing 8·n carbon atoms, R being an n-valent substituted or unsubstituted $C_1$–$C_{34}$ hydrocarbon group, R' being a $C_1$–$C_{20}$ alkyl group and n being a number between 1 and 4; x is between 0.5 and 4.0; and y is between 0.8/n and 2.4/n.

2. A composition according to claim 1, wherein said carboxylic acid alkyl ester $R(COOR')_n$ containing at least 8·n carbon atoms is a carboxylic acid ester, in which R' is a $C_5$–$C_{20}$ alkyl group.

3. A composition according to claim 1, wherein $X^3$ is chlorine.

4. A composition according to claim 1, wherein $X^4$ is chlorine.

5. A composition according to claim 1, wherein x is about 0.7–3.0.

6. A composition according to claim 1, wherein y is 1.0/n–2.4/n, n being 2.

7. A composition according to claim 1, wherein said composition has a composition according to Formula (II):

$$(MgCl_2)_x \cdot TiCl_4 \cdot (Ph(COOR^2)_2)_y \quad (II).$$

8. A composition according to claim 7, which has the approximate Formula (III):

$$(MgCl_2)_{[x]0.5-3.0} \cdot TiCl_4 \cdot (\text{di-}C_8\text{–}C_{14}\text{-alkylphthalate}) \quad (III).$$

9. A composition according to claim 1, wherein said liquid titanium tetrahalide is titanium tetrachloride.

10. A composition according to claim 1, wherein said organic substance S is selected from the group consisting of chlorinated and aromatic hydrocarbons.

11. A composition according to claim 1, wherein said composition is soluble in titanium tetrahalide and/or an organic substance between 60 and 190° C.

12. A composition according to claim 1, wherein the X-ray diffraction spectrum thereof has a halo between 15° and 22° 2theta.

13. A process for the preparation of a composition containing magnesium, titanium, a halogen and a carboxylic acid ester, in which process a complex $MgX^1{}_2 \cdot cR^1OH$, wherein $X^1$ is a halogen, $R^1$ is a $C_1$–$C_{20}$ alkyl group and c is a number between 2.0 and 6.4, a titanium halide $TiX^2{}_4$, wherein $X^2$ is a halogen, and a carboxylic acid ester are contacted and reacted, wherein said composition is prepared in liquid form by using:

(a) as said carboxylic acid ester a carboxylic acid ester having at least 8·n carbon atoms according to Formula (V)

$$R(COOR')_n \quad (V)$$

wherein R is an n-valent substituted or unsubstituted $C_1$–$C_{34}$ hydrocarbon group, R' is a $C_1$–$C_{20}$ alkyl group and n is a number between 1 and 4;

(b) a molar ratio $R(COOR')_n/MgX^1{}_2 \cdot cR^1OH$, which is greater than or equal to about 0.8/n;

(c) a molar ratio $TiX^2{}_4/MgX^1{}_2 \cdot cR^1OH$, which is greater than or equal to about c;

(d) optionally an organic dissolving compound S; and (e) a reaction temperature of between 40° C. and 200° C.

14. A process according to claim 13, wherein $R(COOR')_n$ is a carboxylic acid ester having at least 12 carbon atoms.

15. A process according to claim 14, wherein $R(COOR')_n$ is an α,β-unsaturated carboxylic acid ester.

16. A process according to claim 13, wherein $X^1$ is chlorine.

17. A process according to claim 13, wherein $X^2$ is chlorine.

18. A process according to claim 13, wherein in the complex $MgX^1{}_2 \cdot cR^1OH$, $R^1$ is a $C_1$–$C_{12}$ alkyl, and c in the complex is 2–6.

19. A process according to claim 13, wherein a molar ratio $R(COOR')_n/MgX^1{}_2 \cdot cR^1OH$ is used which is greater than or equal to about 1/n.

20. A process according to claim 13, wherein $R(COOR')_n$ is a compound according to formula $Ph(COOR^2)_2$, wherein Ph stands for ortho-phenylene and $R^2$ stands for a $C_6$–$C_{20}$ alkyl, and the molar ratio $R(COOR')_n/MgX^1{}_2 \cdot cR^1OH$ is between 1/n and 20/n.

21. A process according to claim 13, wherein a molar ratio $TiX^2{}_4/MgX^1{}_2 \cdot cR^1OH$ is used which is greater than or equal to about 1.7·c.

22. A process according to claim 13, wherein a temperature is used which is between about 60° C. and about 140° C.

23. A process according to claim 13, wherein said complex $MgX^1{}_2 \cdot nR'OH$, said titanium tetrahalide $Tix^2{}_4$, and said carboxylic acid ester $R(COOR')_n$ are contacted with an organic compound S which dissolves said reaction product.

24. A process according to claim 23, wherein the molar ratio $TiX^2{}_4/S$ is between 0.5 and 20.

25. A process according to claim 13, wherein:

(a) the complex $MgX^1{}_2 \cdot cR^1OH$, the titanium halide $TiX^2{}_4$ and the optional organic compound S are contacted, whereupon a first contact product is formed;

(b) said first contact product is contacted with said carboxylic acid ester $R(COOR')_n$, whereupon a second contact product is formed.

26. A process according to claim 25, wherein in step (b) the carboxylic acid ester $R(COOR')_n$ is added to the first contact product 10–60 minutes.

27. A process according to claim 26, wherein in step (b), during the adding of the carboxylic acid ester $R(COOR')_n$, the forming second contact product is heated from a temperature of about 20° to a temperature of at least 50° C.

28. A process according to claim 13, which comprises a step after said contacting step, in which step said composition is separated by precipitation.

29. A process according to claim 28, wherein the separation of the composition by precipitation is carried out by cooling a reaction solution in which the composition is in solution mainly in an excess of the titanium halide $TiX^2_4$, whereafter the precipitated composition is separated from the rest of the reaction solution.

30. A process according to claim 28, wherein the separation of said composition by precipitation is carried out by adding to its reaction solution, in which the composition is in solution mainly in an excess of the titanium halide $TiX^2_4$, a precipitating hydrocarbon, whereafter the precipitated composition is separated from the rest of the reaction solution.

31. A composition containing magnesium, titanium, a halogen and a carboxylic acid ester, which has been prepared by a process according to claim 13.

32. A method for the polymerization of ethylenically unsaturated monomer which comprises the polymerization in the presence of a composition according to claim 1.

33. The method according to claim 32, wherein an organometallic compound of a metal of any of groups 1, 2, 12 or 13 (IUPAC 1990) of the Periodic Table of the Elements is used as a cocatalyst.

34. A composition according to claim 1, wherein said carboxylic acid alkyl ester $R(COOR')_n$ containing at least 8·n carbon atoms is an aromatic carboxylic acid $C_6$–$C_{20}$ alkyl ester.

35. A composition according to claim 1, wherein said carboxylic acid alkyl ester $R(COOR')_n$ containing at least 8·n carbon atoms is a phthalic acid di-$C_6$–$C_{20}$ alkyl ester.

36. A composition according to claim 1, wherein said carboxylic acid alkyl ester $R(COOR')_n$ containing at least 8·n carbon atoms is a phthalic acid di-$C_8$–$C_{14}$ alkyl ester.

37. A composition according to claim 1, wherein y is 0.5–1.2, n being 2.

38. A composition according to claim 1, wherein said organic substance S is toluene.

39. A composition according to claim 1, wherein said carboxylic acid alkyl ester $R(COOR')_n$ containing at least 8·n carbon atoms is an α,β-unsaturated carboxylic acid $C_6$–$C_{20}$ alkyl ester.

40. A process according to claim 28, wherein the separation of said composition by precipitation is carried out by adding to its reaction solution, in which the composition is in solution mainly in an excess of the titanium halide $TiX^2_4$, a $C_5$–$C_{10}$ alkane, whereafter the precipitated composition is separated from the rest of the reaction solution.

41. A process according to claim 13, wherein the molar ratio $TiX^2_4/S$ is between 1 and 6.

42. A process according to claim 13, wherein said complex $MgX^1_2.nR'OH$, said titanium tetrahalide $TiX^2_4$, and said carboxylic acid ester $R(COOR')_n$ are contacted with an organic compound S which is toluene.

43. A process according to claim 13, wherein said complex $MgX^1_2.nR'OH$, said titanium tetrahalide $TiX^2_4$, and said carboxylic acid ester $R(COOR')_n$ are contacted with an organic compound S which is a chlorinated hydrocarbon and/or an aromatic hydrocarbon.

44. A process according to claim 13, wherein the reaction temperature is between about 80° C. and about 120° C.

45. A process according to claim 14, wherein $R(COOR')_n$ is an aromatic carboxylic acid $C_6$–$C_{20}$ alkyl ester.

46. A process according to claim 14, wherein $R(COOR')_n$ is a phthalic acid di-$C_6$–$C_{20}$ alkyl ester.

47. A process according to claim 14, wherein $R(COOR')_n$ is a phthalic acid di-$C_8$–$C_{14}$ alkyl ester.

48. A process according to claim 13, wherein a molar ratio $R(COOR')_n/MgX^1_2.cR^1OH$ is used which is between 1/n and 20/n.

49. A process according to claim 13, wherein a molar ratio $TiX^2_4/MgX^1_2.cR^1OH$ is used which is between 10 and 100.

50. A process according to claim 13, wherein a molar ratio $TiX^2_4/MgX^1_2.cR^1OH$ is used which is between 20 and 50.

* * * * *